United States Patent
Kämpf et al.

(10) Patent No.: US 11,440,337 B2
(45) Date of Patent: Sep. 13, 2022

(54) PEN

(71) Applicant: STABILO International GmbH, Heroldsberg (DE)

(72) Inventors: Karl-Peter Kämpf, Röttenbach (DE); Harald Winkler, Fürth (DE)

( * ) Notice: Subject to any disclaimer, the term of this patent is extended or adjusted under 35 U.S.C. 154(b) by 371 days.

(21) Appl. No.: 16/615,797

(22) PCT Filed: May 16, 2018

(86) PCT No.: PCT/EP2018/062782
§ 371 (c)(1),
(2) Date: Nov. 21, 2019

(87) PCT Pub. No.: WO2018/215264
PCT Pub. Date: Nov. 29, 2018

(65) Prior Publication Data
US 2020/0094613 A1   Mar. 26, 2020

(30) Foreign Application Priority Data
May 22, 2017   (DE) .......................... 2020170027186

(51) Int. Cl.
*B43K 29/08*   (2006.01)
*B43K 7/00*   (2006.01)
(Continued)

(52) U.S. Cl.
CPC .............. *B43K 29/08* (2013.01); *B43K 7/005* (2013.01); *A61B 5/1125* (2013.01); *A61B 5/225* (2013.01);
(Continued)

(58) Field of Classification Search
CPC ...... B43K 29/08; B43K 29/00; B43K 29/003; B43K 29/087; B43K 7/005; B43K 23/008; B43K 23/012; B43K 23/016; B43K 23/00; A61B 5/1125; A61B 5/225; A61B 2560/0247
(Continued)

(56) References Cited

U.S. PATENT DOCUMENTS

| 5,018,208 A | 5/1991 | Gladstone |
| 5,774,571 A | 6/1998 | Marshall |

(Continued)

FOREIGN PATENT DOCUMENTS

| AT | 515976 A1 | 1/2016 |
| CN | 1307709 A | 8/2001 |

(Continued)

OTHER PUBLICATIONS

European Patent Office, International Search Report for International Application No. PCT/EP2018/062782, dated Oct. 7, 2018.
(Continued)

*Primary Examiner* — David J Walczak
(74) *Attorney, Agent, or Firm* — Bradley Arant Boult Cummings LLP; Timothy L. Capria; Alexandra C. Lynn

(57) ABSTRACT

A pen comprising a shaft, a gripping zone, and a measuring device having a sensor configured to measure a force acting on the gripping zone. The pen further comprises a cover in the area of the gripping zone, the cover configured to cover the measuring device.

20 Claims, 11 Drawing Sheets

(51) Int. Cl.
  *B43K 23/008* (2006.01)
  *B43K 23/012* (2006.01)
  *A61B 5/11* (2006.01)
  *A61B 5/22* (2006.01)

(52) U.S. Cl.
  CPC .............. *A61B 2560/0418* (2013.01); *A61B 2562/0247* (2013.01); *B43K 23/008* (2013.01); *B43K 23/012* (2013.01)

(58) Field of Classification Search
  USPC .......................................................... 401/6–8
  See application file for complete search history.

(56) References Cited

U.S. PATENT DOCUMENTS

| | | | |
|---|---|---|---|
| 6,158,910 A * | 12/2000 | Jolly | ................ B25G 1/102 |
| | | | 16/430 |
| 7,454,977 B2 | 11/2008 | Larsen et al. | |
| 2003/0076310 A1 | 4/2003 | Kanzaki | |
| 2004/0126175 A1 * | 7/2004 | Willat | ................ B43K 23/004 |
| | | | 401/6 |
| 2009/0044640 A1 | 2/2009 | Vassilev | |
| 2017/0138808 A1 | 5/2017 | Tham et al. | |
| 2018/0058954 A1 | 3/2018 | Kihara et al. | |

FOREIGN PATENT DOCUMENTS

| | | |
|---|---|---|
| CN | 101901063 A | 12/2010 |
| CN | 102736747 A | 10/2012 |
| CN | 203511051 U | 4/2014 |
| CN | 103995590 A | 8/2014 |
| CN | 106218273 A | 12/2016 |
| DE | 202007002778 U1 | 4/2007 |
| EP | 2182423 A2 | 5/2010 |
| FR | 2805211 | 8/2001 |
| WO | 1999052060 A2 | 10/1999 |
| WO | 2007003417 A2 | 1/2007 |
| WO | 2011141734 A1 | 11/2011 |
| WO | 2015150154 A1 | 10/2015 |
| WO | 2016194690 A1 | 12/2016 |

OTHER PUBLICATIONS

European Patent Office, Written Opinion of the International Searching Authority for International Application No. PCT/EP2018/062782, dated Oct. 7, 2018.

* cited by examiner

PEN

The invention relates to a pen with a shaft, a gripping zone and a measuring device having a sensor, said measuring device measuring a force acting on the gripping zone.

Pens of the type mentioned above are known, for example, from EP 2 182 423 A2. In the known pen, a pressure sensor for measuring radial pressures is located in the gripping zone. There, it does not only look unpleasing to the eye, it also has a negative impact on the haptics. The same applies to the pressure sensor configured in the form of a fluid-carrying helix according to WO 2007/003417 A2.

The invention is based on the object to develop the pen of the type mentioned above further in such a way that the measuring device having the sensor no longer interferes negatively with both the optics and the haptics.

According to the invention, this object is achieved by a cover in the area of the gripping zone which covers the measuring device on the outside.

By this cover, the optical appearance of the pen, in particular in the gripping zone, can be chosen independent of the configuration of the measuring device having the sensor. The same applies to the haptics because, according to the invention, the haptics is determined by the cover and not by the measuring device.

Preferably, it is provided, that the cover is in the form of a sleeve, which surrounds a shaft of the pen at least partially. This configuration is especially advantageous in particular with respect to simplicity of manufacturing.

According to the invention, the measuring device has further preferably a gear unit, which transfers a first movement originating from a force acting on the gripping zone to the sensor.

In other words, according to this configuration, it is provided that the force acting on the gripping zone is not transferred directly to the sensor, rather a gear unit is interposed allowing for the configuration of the direction and magnitude of the force acting on the sensor according to respective circumstances, as appropriate. Further, the sensor can thereby be arranged at a position where it adds little to the thickness such that the gripping zone does not become too thick.

In this context, according to the invention, it is further provided preferably that the gear unit transmits the first movement to a second movement directed transversely to the first movement and captured by the sensor, by means of a ramp, wherein the angle of attack ($\varphi$) of the ramp determines the gear ratio This offers the possibility of setting the measuring sensitivity by appropriately choosing the angle of attack of the ramp.

According to a particular preferred embodiment of the invention it is provided that the gear unit has means for limiting the force transmitted to the sensor.

This configuration ensures that the sensor is not exposed to excessive force thereby protecting it from damage. In particular, it is protected from peak loads.

According to the invention, the limitation device further preferably has a resilient tongue. This constitutes an especially simple implementation.

According to the invention, for further protecting the sensor, it can be provided that the sensor, in response to the force transferred to it by the gear unit, can get out of the way against an elastic restoring force.

A particularly preferred embodiment of the invention provides that the shaft is at least partially part of the gear unit.

In other words, an additional function is assigned to the shaft, namely that it (at least partially) serves to transfer the force acting on the gripping zone to the sensor. In doing so, the number of parts can be kept low.

It can be provided, for example, that the outer contour of the shaft, in response to a force acting on the gripping zone, adjusts against an elastic restoring force, wherein the sensor responds to the adjustment In other words, in this configuration the shaft is deformed by a force acting on the gripping zone, wherein the deformation acts on the sensor.

Finally, according to the invention, it is also particularly preferably provided that the gripping zone, viewed in the circumferential direction of the pen, is in a different angle range than the sensor and/or the gear unit.

It is therefore particularly easy to transform a force acting on the gripping zone into a movement, which is translated by the gear unit to a force acting on the sensor.

Below, the invention is explained in more detail by preferred exemplary embodiments with reference to the appended drawing.

Figure 1:
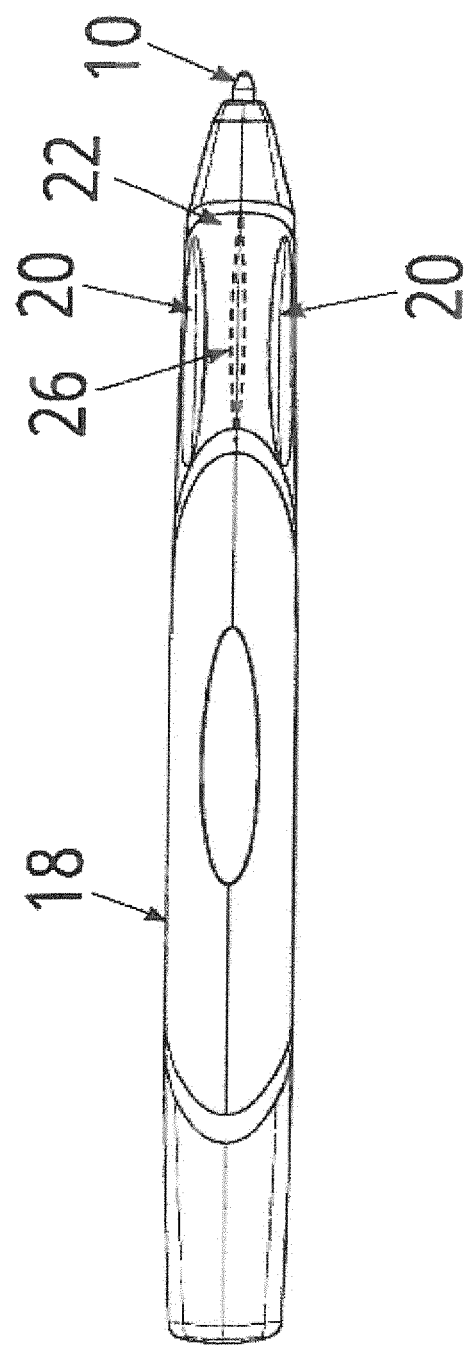
FIG. 1 shows a schematic side view of an exemplary embodiment of the pen according to the invention.
Figure 2:
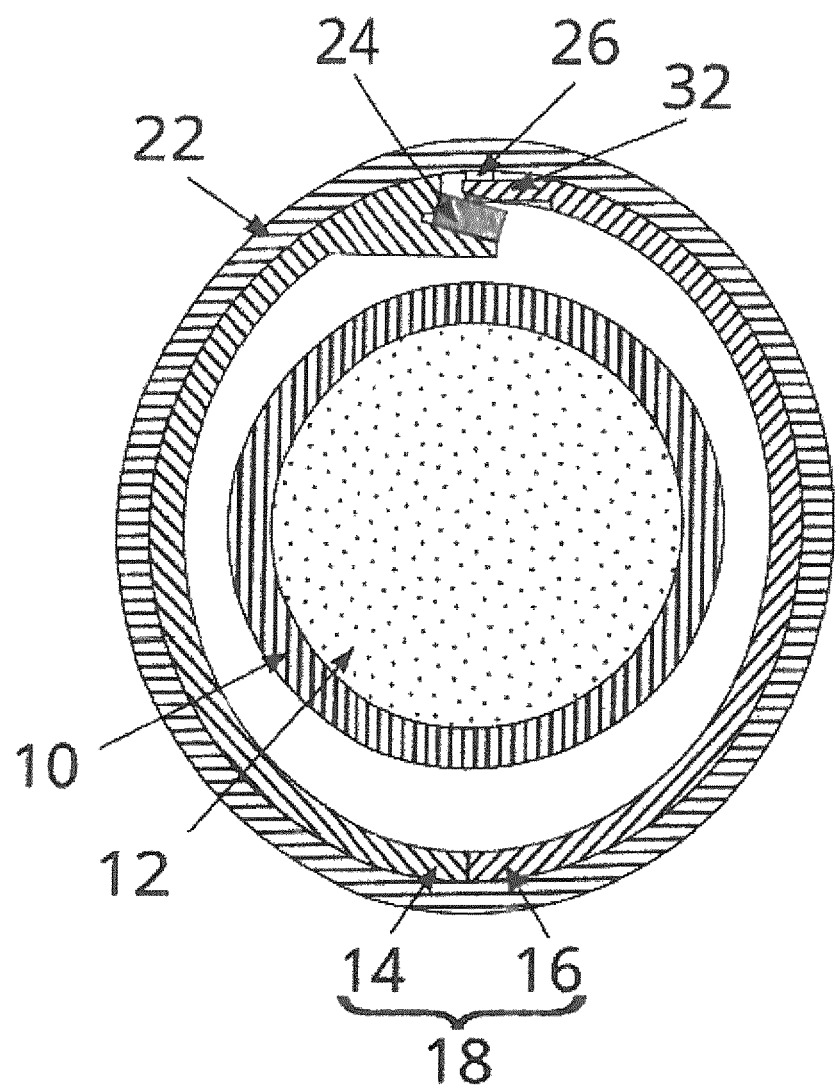
FIG. 2 shows a schematic cross-sectional view of the pen of FIG. 1
Figure 3:
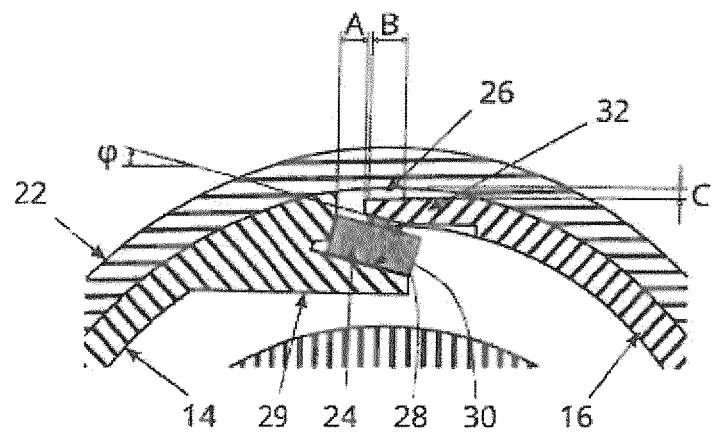
FIG. 3 shows a schematic enlarged partial view of FIG. 2.
Figure 4:
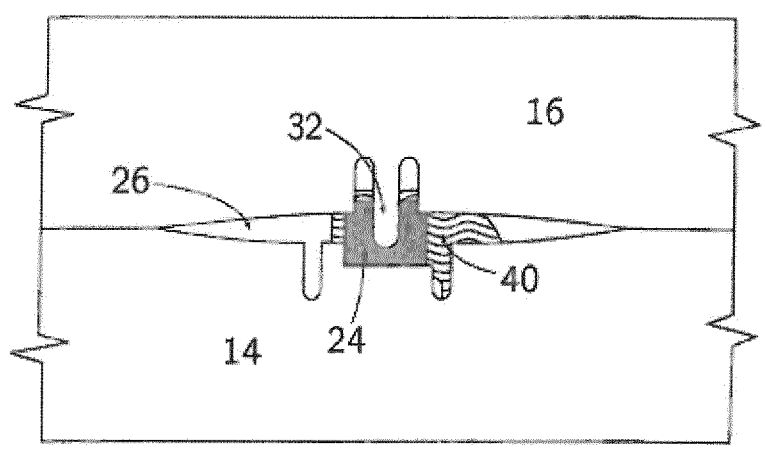
Figure 5:
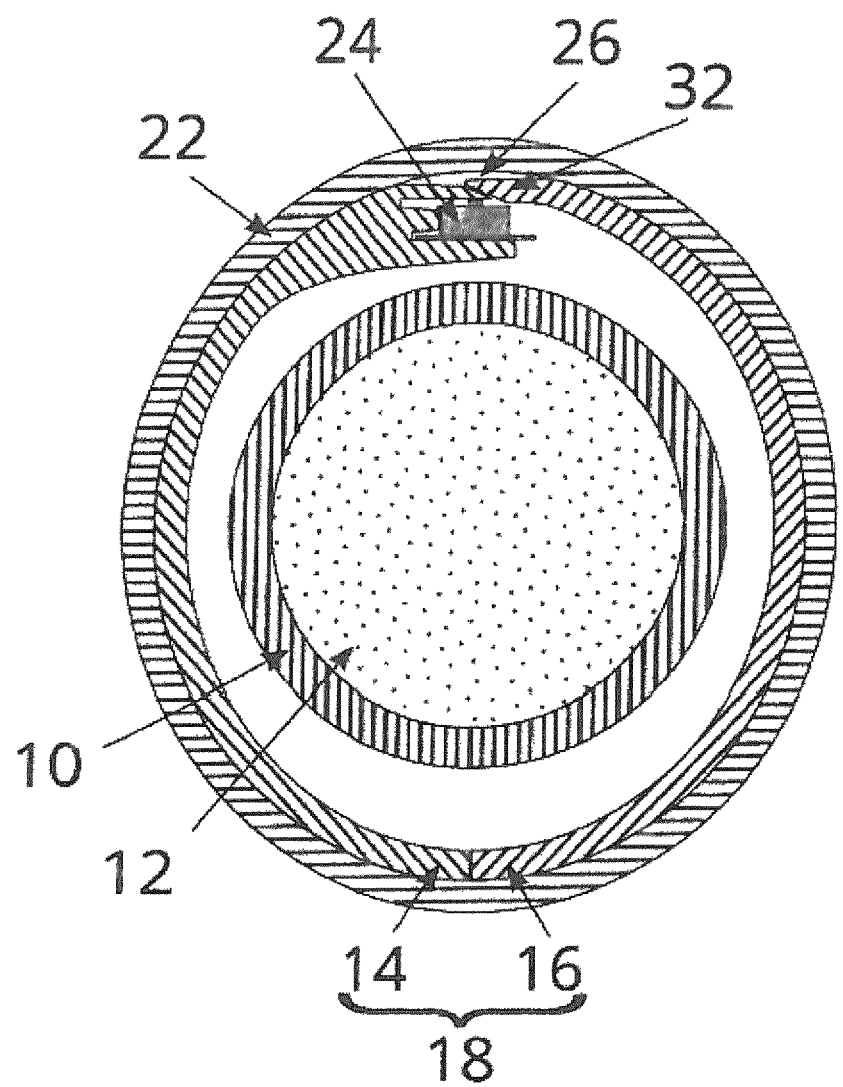
Figure 6:
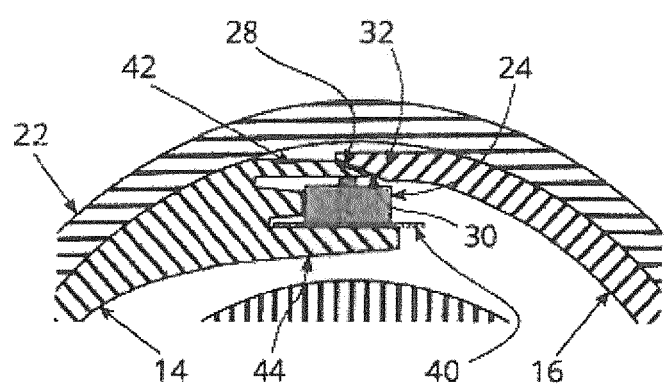
Figure 7:
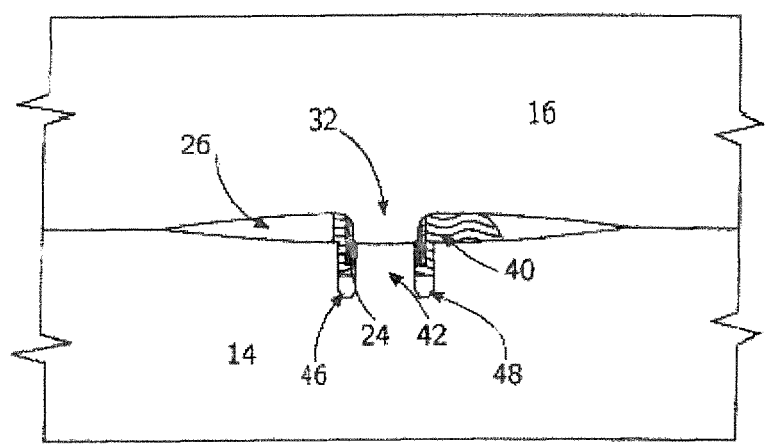
Figure 8:
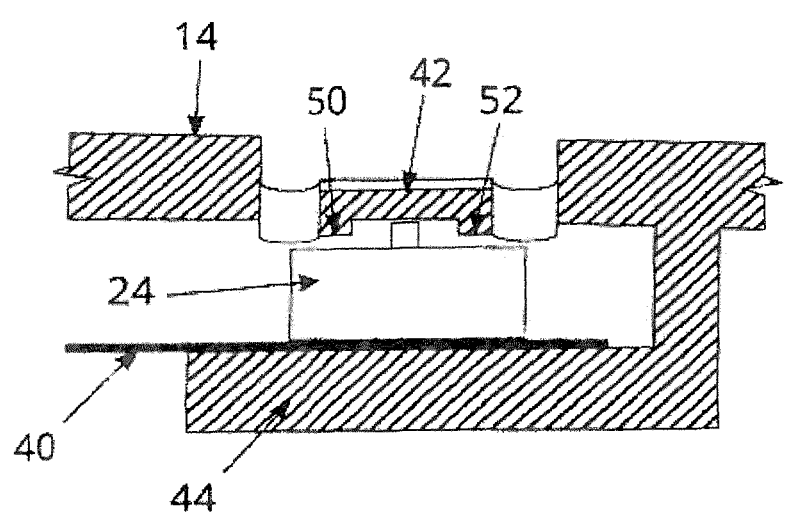
Figure 9:
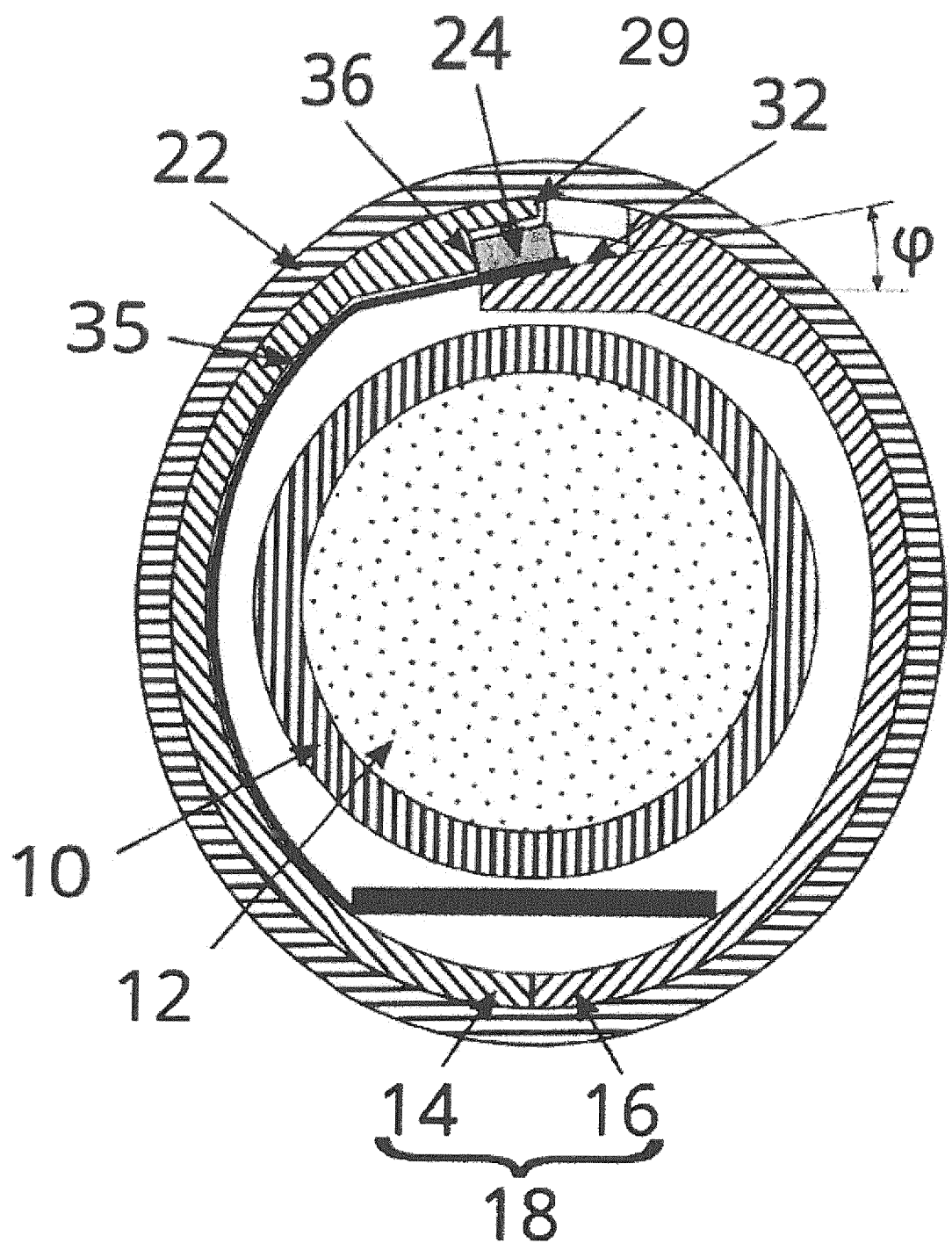
Figure 10:
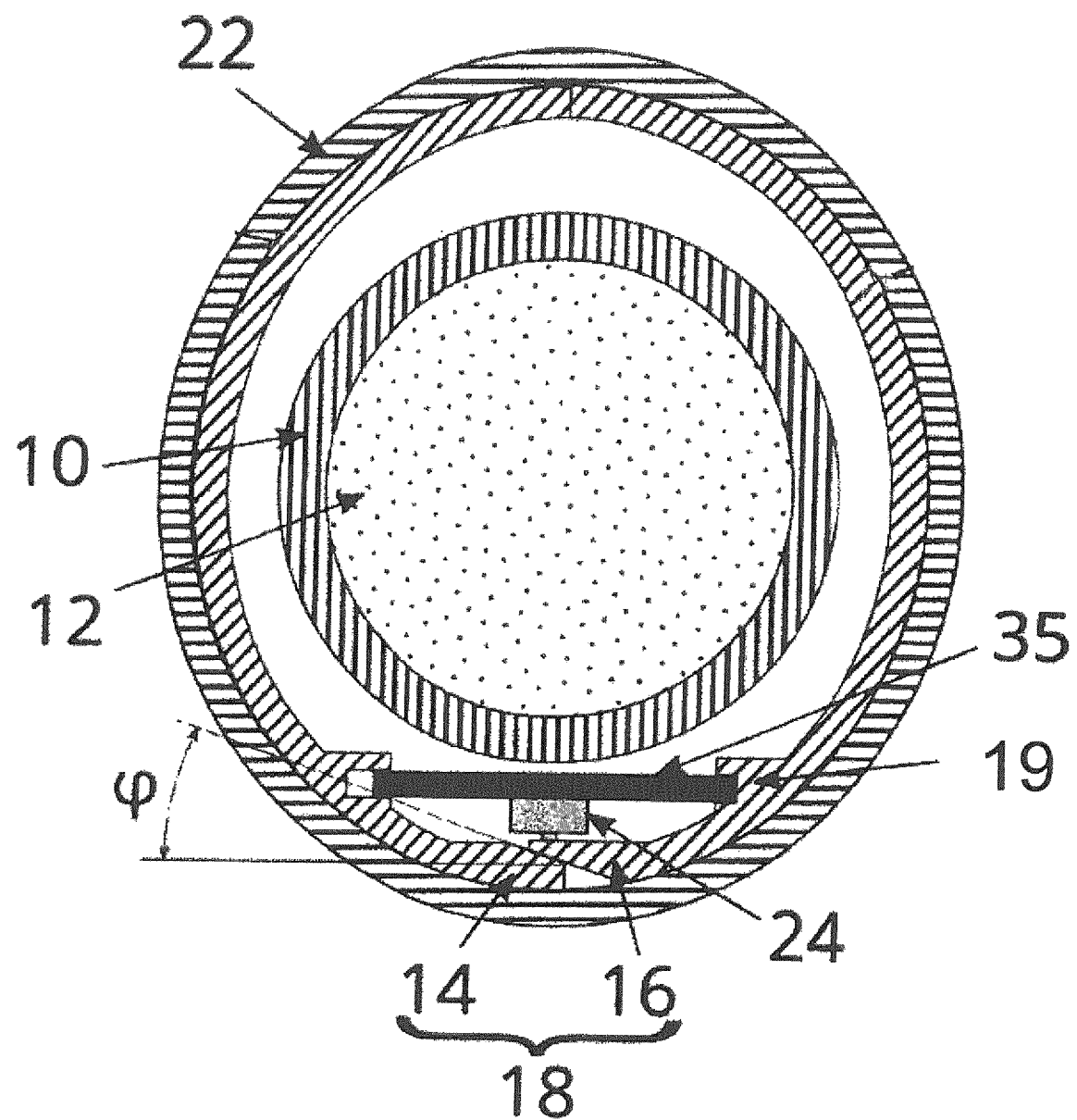
Figure 11:
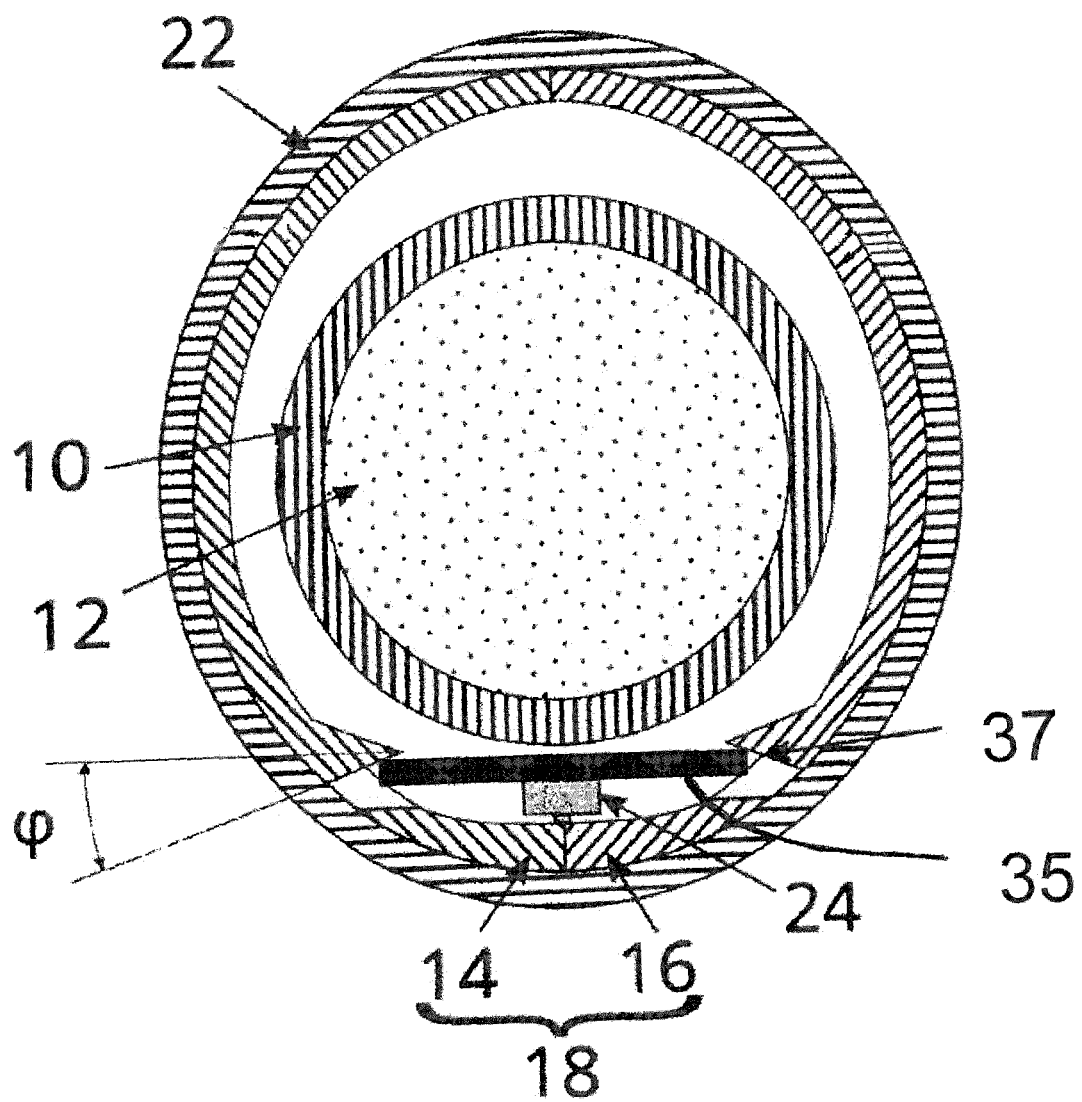

FIG. 4 shows a schematic, enlarged top view of FIGS. 2 and 3, however without sleeve, FIGS. 5 to 7 show the same views as FIGS. 2 to 4, however, from a different exemplary embodiment, FIG. 8 shows a schematic sectional view near the median plane of the embodiment of FIGS. 4 to 7, FIG. 9 shows the same view as FIG. 1, but from a third exemplary embodiment, and FIGS. 10 and 11 show the same views as FIG. 1, but from fourth and fifth exemplary embodiments.

The exemplary embodiment of the pen according to the invention of FIGS. 1 to 4 includes a refill tube 10 with an ink filling 12, a shaft 18 having two half shells 14 and 16 with a gripping zone 20 and a sleeve 22 covering the shaft 18 in the area of the gripping zone 20.

A force sensor 24 is used to determine the radial force acting on the gripping zone 20.

The sleeve 22, over part of its length, is pushed on the shaft 18. In the area of the gripping zone 20, the shaft 18 is recessed along one of the joining lines such that the two half shells 14, 16 can be pushed together in this area. In FIG. 1, the recess is indicated by a dashed line and designated by reference numeral 26

The shaft 18 and the sleeve 22 in each case are made of elastically deformable material, which is why they allow for elastic deformation which is used for force measurement.

As explained in more detail below, the deformation of the sleeve 22 carrying the gripping zone 20 and shaft 18 takes place in a direction away from the force sensor 24, such that this deformation does not affect the measuring process. The gripping zone 20 on the one hand and the sensor 24 on the other hand, are located in different angle ranges when viewed in the circumferential direction of the pen. They are separated by an angle of about 90°.

The sensor 24 is inclined relative to the radial direction. By setting the angle of inclination $\varphi$, the sensitivity can be determined, i.e., the extent of pressure on the sensor 24 as a result of a deformation of the sleeve 22 in the gripping zone.

For this purpose, the sensor 24 is attached to a ramp 28 of a tongue 29 of the half shell 14. A corresponding ramp 30 is attached to a resilient tongue 32 of the half shell 16.

Referring to FIG. 3, the recess 26 has a width B, and the resilient tongue 32 is, when no pressure is applied to the gripping zone 20, at a distance A from the half shell 14. This distance A determines the maximum possible deformation before the resilient tongue 32 hits the half shell 14. The smaller of the two dimensions A and B determines the maximum load on the sensor 24. Advantageously, the distance A is smaller than the width B. As already mentioned above, the inclination of the sensor 24, i.e., the angle φ, is the extent of which a deformation of the shaft 18 exerts a force on the sensor 24. Since both the tongue 29 and the resilient tongue 32 that is pushing on the sensor 24 when under load, are designed as flexural members, their deformation can additionally limit the load acting on the sensor 24, in particular as long as the distance C between the resilient tongue 32 and the sleeve 22 is not zero. This is facilitated by the deformation of the sleeve 22, which, in the case of axial pressure on the gripping zone 20, i.e., forming both sides in FIG. 2, will bulge upward and downward.

The two half shells 14, 16 of the shaft 18 with the tongues 29 and 32 for a gear unit which transmits forces acting on the gripping zone 20 to the sensor 24.

In addition to the elements described above, FIG. 4 shows a flex element 40, which connects the sensor 24 to an evaluation electronics (not shown). By means of this electronics, the signals emitted by the sensor 24 can be evaluated.

The assembly of the pen is carried out as follows: First, the sensor 24 is glued to the ramp 28 of the half shell 14. Then, the half shell 16 is fitted. Pushing on the sleeve 22 completes the structure.

The exemplary embodiment according to FIGS. 5 to 8 differs from the above-described exemplary embodiment in particular in that the sensor 24 is not inclined. Instead, there is a tongue 42 between the resilient tongue 32 and the sensor. It has a flexible design by lateral slots 46, 48, cf. FIG. 8. The sensor 24 is supported by a rigid base 44. It is positioned on flex element 40. In this exemplary embodiment, the ramp 28 is formed on the flexible tongue 42.

Particularly FIGS. 5 and 6 illustrate the mounting of the sensor 24 in the shape of forceps in the case of this exemplary embodiment. The rigid base 44 holds the sensor 24, and the flexible tongue 42 pushes on the sensor 24 when the resilient tongue 32 by the ramps 30 and 28 pushes the flexible tongue 42 in FIGS. 5 and 6 downward upon compression of the sleeve 22 in the gripping zone 20.

The bottom (not shown) of the resilient tongue 32 is configured so that it goes solid with the sensor 24 before the measuring pin of the sensor 24 is pushed in too deep. By means of the angle of the ramp 30 with which the half shell 16 presses on the half shell 14, the gear ratio can be set when measuring the force. With increasing deformation the ramp 30 pushes on the ramp 28 and thereby presses on the sensor 24. This is facilitated by the deformation of the sleeve 22, which will bulge upward and downward at an axial pressure on the grip zone 20.

FIGS. 7 and 8 illustrate the lateral slots 46, 48, by means of which the rigidity of the flexible tongue 42 is reduced.

FIG. 8 shows strips 50, 52 which limit the indentation depth of the measuring pin of the sensor 24 to a given extent, because at overload they release the pressure in the housing of the sensor 24.

In contrast to the exemplary embodiment of FIGS. 2 to 4, according to FIGS. 5 to 8 no sliding movement occurs on the sensor 24, rather only between the tongue 42 with the ramp 28 on the one hand and the tongue 32 with the ramp 30 on the other hand. This serves to reduce the wear and tear and the freedom of choice of the materials involved in sliding. In particular, the sensor 24 is subject to certain specifications, because it must withstand the prevailing temperatures during soldering and therefore comprises comparatively hard materials in contrast, for example, to the comparatively soft half shells 14 and 16.

In the third embodiment shown in FIG. 9, the shaft of the pen consists of a split case with two halves, where a grip area is slid over a portion of the length of the shaft. In the portion of the grip area (shaded in FIG. 1), the shaft is recessed along one of the seams, such that the two halves of the split case can be compressed in this portion. The recess is indicated by a dashed line in the top view, cf. FIG. 1. The use of flexible materials for the shaft and the grip area allows for a reversible deformation, which is utilized for the force measurement. At the same time, the shape of the recess limits the maximum deformation of the sensor, which prevents an overload of the sensor. The deformation of the grip area occurs in a direction away from the force sensor, such that this deformation cannot impede the measuring process.

FIG. 9 shows how the sensor 24 is mounted as if between a pair of pincers. The sensor is mounted on a flexible carrier 35, which also supports the electrical connections, and sits in a recess 36 in the left half 14 of the shaft 18. A resilient tongue 32—which pushes the sensor upward when the grip zone is compressed—protrudes from the opposite half of the shaft. The components are:

24 Force sensor
14 Left half of the shaft
22 Slip-on grip area or sleeve
10 Tube (Ink cartridge)
12 Ink
29 Resilient tongue or blade on the left half of the shaft
32 Resilient tongue or blade on the right half of the shaft
16 Right half of the shaft
35 Flexible carrier
φ Angle of inclination As the deformation increases, the right side of the ramp pushes underneath the underside of the flexible carrier 35, thereby pushing the sensor upward. This is aided by the deformation of the grip area, which bulges upwardly and downwardly when pressure is applied from the sides, which facilitates the overlapping movement of the two halves of the shaft. The sloped upper side of the tongue on the right half of the shaft determines the degree to which the deformation of the halves of the shaft translates into movement of the sensor.

It is advantageous that resilient tongue 32 does not slide on force sensor 24, but on carrier 35.

During assembly, the sensor first is inserted into the left half of the shaft before the right half of the shaft is set on top of the left half. Sliding on the grip area completes the assembly.

The flexibility of the halves of the shaft can be adjusted via notches.

The embodiment shown in FIG. 10 dispenses with the arm on the flexible plate and use the sensor plate itself to house the force sensor. For this design, the carrier 35 also must allow the movement of the two halves 14 and 16 of the shaft relative to each other, as shown in FIG. 10. To that end, the carrier is mounted to the right half in a fixed position 19, while being free to move in a slot in the left half. The pressure on the grip is designed to move the two halves toward each other, whereby the wedge-shaped overlap at the lower joint results in a vertical force being exerted upon the measuring pin of the sensor 24. The unilaterally fixed mounting of the plate thereby ensures that any gliding movements only occur between the two halves 14 and 16 of the shaft and not between the measuring pin and the shaft.

In the embodiment shown in FIG. 11, the carrier moves relative to the shaft, which is why the design looks very different, Instead of a gap between the two halves of the shaft, the flexibility in this design stems from a U-shaped groove which forms two pressure surfaces, which can be compressed against the spring stiffness of the plastic material. On the inside, the two surfaces push against the sensor carrier 35 via two wedges 37, while the force sensor 24 is soldered to the underside of the sensor carrier 35. As the wedge-shaped teeth on the interior side of the pressure surfaces push the carrier downward, they push the sensor pin against the lower side of the shaft 14 and 16.

This design distinguishes itself by a particularly simple installation of the force sensor.

The degree to which the deformation of the shaft translates into movement of the measuring pin on the sensor here too can be adjusted via the angle φ.

In summary, it should be noted that the invention comprises the following features which individually and in any combination can be essential for the realization of the invention in its various embodiments:

The pushed on sleeve 22 covers the measuring mechanism to the outside.

A change in the inclination of the sensor 24 or the angle of attack of the ramps 28, 30 offers the possibility to set the measuring sensitivity.

The resilient tongue 32 limits the force exerted on the sensor 24.

The sensor 24 is supported elastically. It is hidden in the wall of the shaft 18, whereby the increase in thickness of the sleeve 22 or the gripping zone 20 can be kept low.

The pen can be readily assembled.

What is claimed is:

1. A pen, comprising:
    a gear unit comprising a shaft, the shaft including a ramp,
    a gripping zone located on the shaft and having a gripping zone area,
    a measuring device located on the ramp, the measuring device including a sensor configured to measure a force acting on the gripping zone, and
    a cover in the gripping zone area, the cover configured to cover at least a portion of the measuring device,
    wherein the gear unit is configured to transfer a first movement originating from the force acting on the gripping zone to the sensor and to translate the first movement to a second movement directed transversely to the first movement and captured by the sensor via the ramp, and
    wherein an angle of attack (φ) of the ramp determines a gear ratio.

2. The pen according to claim 1, wherein the cover has a shape of a sleeve at least partially surrounding the shaft.

3. The pen according to claim 1, wherein the gear unit has a limitation device to limit the force transferred to the sensor.

4. The pen according to claim 3, wherein the limitation device has a resilient tongue.

5. The pen according to claim 1, wherein the sensor, in response to the force transferred to it by the gear unit, is configured to move away against an elastic restoring force.

6. The pen according to claim 1, wherein the ramp and the measuring device are at least partially inside of the shaft.

7. The pen according to claim 6, wherein the shaft comprises an outer contour configured to, in response to a force acting on the gripping zone, adjust against an elastic restoring force, wherein the sensor responds to the adjustment.

8. The pen according to claim 7, wherein the shaft is deformed by the force acting on the gripping zone.

9. The pen according to claim 1, wherein the gripping zone, when viewed in a circumferential direction of the pen, is in a different angle range than the sensor or the gear unit.

10. The pen according to claim 9, wherein the gripping zone, when viewed in a circumferential direction of the pen, is in a different angle range than the sensor and the gear unit.

11. The pen according to claim 1, wherein the shaft is deformed by the force acting on the gripping zone.

12. The pen according to claim 1, wherein the sensor comprises a measuring pin configured to be depressed by the gear unit in response to the force acting on the gripping zone.

13. The pen according to claim 12, wherein the force acting on the gripping zone deforms the cover, and wherein the deformation of the cover causes the gear unit to depress the measuring pin.

14. The pen according to claim 1, further comprising an evaluation electronic and a flex element connecting the sensor to the evaluation electronic, wherein the evaluation electronic is configured to evaluate signals emitted by the sensor in response to the force acting on the gripping zone.

15. The pen according to claim 14, wherein the sensor is positioned on at least a portion of the flex element.

16. The pen according to claim 1, herein the shaft comprises an elongated tube.

17. The pen according to claim 16, wherein the shaft is comprised of two half shells affixed together.

18. The pen according to claim 17, wherein each of the two half shells has a tongue that projects into the elongated tube, and wherein the ramp is located on one of the tongues.

19. The pen according to claim 1, wherein the shaft is recessed in the gripping zone area.

20. The pen according to claim 1, wherein the shaft and the cover are comprised of an elastically deformable material.

* * * * *